(12) United States Patent
Bogineni et al.

(10) Patent No.: US 11,717,257 B2
(45) Date of Patent: Aug. 8, 2023

(54) FETAL ULTRASOUND MONITORING METHOD AND SYSTEM

(71) Applicant: General Electric Company, Schenectady, NY (US)

(72) Inventors: Kiran Kumar Bogineni, Bangalore (IN); Ravi Jaiswal, Bangalore (IN); Shruti Gadgil, Bangalore (IN); Jay Mehta, Bangalore (IN)

(73) Assignee: General Electric Company, Schenectady, NY (US)

( * ) Notice: Subject to any disclaimer, the term of this patent is extended or adjusted under 35 U.S.C. 154(b) by 627 days.

(21) Appl. No.: 15/877,003

(22) Filed: Jan. 22, 2018

(65) Prior Publication Data

US 2019/0223832 A1     Jul. 25, 2019

(51) Int. Cl.
*A61B 8/08*         (2006.01)
*A61B 5/00*         (2006.01)
(Continued)

(52) U.S. Cl.
CPC ........ *A61B 8/0866* (2013.01); *A61B 5/02411* (2013.01); *A61B 5/4362* (2013.01); *A61B 8/429* (2013.01); *A61B 8/4254* (2013.01); *A61B 8/4444* (2013.01); *A61B 8/465* (2013.01); *A61B 5/344* (2021.01); *A61B 8/02* (2013.01);
(Continued)

(58) Field of Classification Search
CPC ....... A61B 8/0866; A61B 8/429; A61B 8/465; A61B 8/4444; A61B 8/4254; A61B 5/4362; A61B 5/02411; A61B 8/4477; A61B 8/4438; A61B 8/4483; A61B 8/4281; A61B 5/0444; A61B 2503/02; A61B 8/02; A61B 8/4272; A61B 8/42; A61B 8/4245; A61B 8/4236; A61B 5/4343; A61B 5/4356
See application file for complete search history.

(56) References Cited

U.S. PATENT DOCUMENTS 5,465,724 A * 11/1995 Sliwa, Jr. ................. A61B 8/12
                                                                                                    600/459
6,106,464 A      8/2000 Bass
(Continued)

OTHER PUBLICATIONS

PCT/US2019/014507—International Search Report/Written Opinion dated May 1, 2019; 12 pages.
(Continued)

*Primary Examiner* — Luther Behringer
*Assistant Examiner* — Amy Shafqat
(74) *Attorney, Agent, or Firm* — Andrus Intellectual Property Law, LLP

(57) ABSTRACT

A method of fetal ultrasound monitoring includes detecting contact of a first ultrasound transducer to a mother's abdomen based on input from a contact sensor in the first ultrasound transducer. A first transducer ID is received from the first ultrasound transducer, and then the first transducer ID is correlated with a first transducer label. A first heart rate is measured based on output of an ultrasound device in the first ultrasound transducer, and a heart rate indicator is displayed accordingly. A position of the first ultrasound transducer is identified in a two-dimensional plane, and the first transducer label is displayed on an abdomen image based on the first position.

14 Claims, 10 Drawing Sheets

(51) Int. Cl.
  *A61B 5/024* (2006.01)
  *A61B 8/00* (2006.01)
  *A61B 8/02* (2006.01)
  *A61B 5/344* (2021.01)

(52) U.S. Cl.
  CPC .......... *A61B 8/4281* (2013.01); *A61B 8/4438* (2013.01); *A61B 8/4477* (2013.01); *A61B 8/4483* (2013.01); *A61B 2503/02* (2013.01)

(56) References Cited

U.S. PATENT DOCUMENTS

| | | | |
|---|---|---|---|
| 2004/0171935 A1 | 9/2004 | Van Creveld | |
| 2004/0236193 A1* | 11/2004 | Sharf | A61B 5/1127 600/302 |
| 2007/0260155 A1 | 11/2007 | Rapoport | |
| 2009/0247877 A1* | 10/2009 | Tanaka | A61B 8/4427 600/462 |
| 2010/0191121 A1* | 7/2010 | Satoh | A61B 8/56 600/459 |
| 2011/0112403 A1* | 5/2011 | Machtey | A61B 8/4477 600/443 |
| 2011/0237906 A1* | 9/2011 | Kabakov | G16H 40/63 600/301 |
| 2012/0150010 A1* | 6/2012 | Hayes-Gill | A61B 5/4343 600/382 |
| 2016/0270675 A1* | 9/2016 | Oz | A61B 5/6823 |
| 2017/0273664 A1 | 9/2017 | Baym | |
| 2017/0303899 A1 | 10/2017 | Willsie | |
| 2018/0000405 A1* | 1/2018 | Penders | A61B 5/1118 |
| 2019/0133549 A1* | 5/2019 | Hamelmann | A61B 8/4245 |

OTHER PUBLICATIONS

EP application 19741600.1 filed Jul. 20, 2020—Extended Search Report dated Jul. 30, 2021, 5 pages.

* cited by examiner

FETAL ULTRASOUND MONITORING METHOD AND SYSTEM

BACKGROUND

The present disclosure generally relates to a method and system for fetal ultrasound monitoring, and more specifically to a fetal ultrasound monitoring system and method that tracks and displays position of fetal ultrasound transducers.

Fetal ultrasound monitoring of infant heart rate is a common infant monitoring technique to monitor and track an infant's health and current condition. Infant heart rate monitoring via a fetal ultrasound monitor, also known as cardiotocography (CTG), is a common technical means of recording fetal heartbeat and to assess fetal wellbeing, such as before or during labor. Such fetal heart rate monitoring typically occurs over a relatively long monitoring period, often lasting several hours or more. The monitoring period may be continuous, or may be several intermittent monitoring periods where the fetal heart rate is calculated from fetal heart motion measured by ultrasound.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of fetal ultrasound monitoring includes detecting contact of a first ultrasound transducer to a mother's abdomen based on input from a contact sensor in the first ultrasound transducer. A first transducer ID is received from the first ultrasound transducer, and then the first transducer ID is correlated with a first transducer label. A first heart rate is measured based on output of an ultrasound device in the first ultrasound transducer, and a heart rate indicator is displayed accordingly. A position of the first ultrasound transducer is identified in at least a two-dimensional plane, and the first transducer label is displayed on an abdomen image based on the first position.

In one embodiment, a fetal ultrasound system includes one or more fetal ultrasound transducers, a monitor, and a display device. Each fetal ultrasound transducer includes an ultrasound device configured to generate soundwaves in the ultrasonic range and convert reflected soundwaves into ultrasound data for detecting a fetal heartbeat. Each fetal ultrasound transducer further includes a contact sensor configured to sense contact with a mother's abdomen and generate a contact indicator. Each ultrasound transducer also includes a transducer identifier unit that communicates a transducer ID. The monitor is configured to receive the ultrasound data, the contact indicator, and the transducer ID from the one or more ultrasound transducers. The monitor comprises a transducer tracking module software executable on a processor to generate a transducer label for each of the one or more fetal ultrasound transducers and associate the transducer ID for each fetal ultrasound transducer with the respective transducer label. A fetal heartrate is determined based on the ultrasound data and a corresponding heart rate indicator is determined. A position of each of the one or more fetal ultrasound transducers is identified. An abdomen image is generated with transducer labels positioned thereon based on the position of each of the one or more fetal ultrasound transducers. A display device is configured to display the abdomen image with the transducer label for each of the one or more fetal ultrasound transducers, and to display the fetal heart rate indicator in association with the respective transducer label.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their research and experience in the relevant field, the present inventors have recognized that challenges currently exist in the field of fetal heart rate monitoring relating to consistently tracking a fetal heart rate over a long monitoring period, such as spanning several hours. For example, mothers often require disconnection from a fetal heart rate monitor, such as to use the restroom, take a bath, etc. When the mother returns and is reconnected to the fetal heart rate monitor, positioning of the fetal ultrasound transducer on the mother's abdomen must be re-performed, as there is no tracking of placement of the ultrasound transducers from the previous monitoring session. Moreover, this problem is exaggerated in the case of multiples—e.g., twins, triplets, or more—where there is no way for clinicians to identify how the transducers were arranged on the mother's abdomen and which fetal ultrasound transducer was associated with which baby. Accordingly, transducer often get swapped, and thus the heartbeat tracings between monitoring sessions are not properly compared and the reliability and accuracy of fetal heart rate monitoring over the entire monitoring period is compromised.

Upon recognition of the foregoing problems and challenges in the relevant art of fetal heart rate monitoring, the inventors developed the disclosed system and method that allows position tracking of fetal heart rate transducers, such as between monitoring periods or between entirely separate monitoring sessions (e.g., conducted during different visits). The disclosed system and method identify the position of each ultrasound transducer attached to the mother's abdomen and associate a transducer ID provided by each fetal ultrasound transducer with the corresponding position. The system further creates and displays an abdomen image with transducer labels positioned thereon based on the position of each of the one or more fetal ultrasound transducers.

Figure 1:
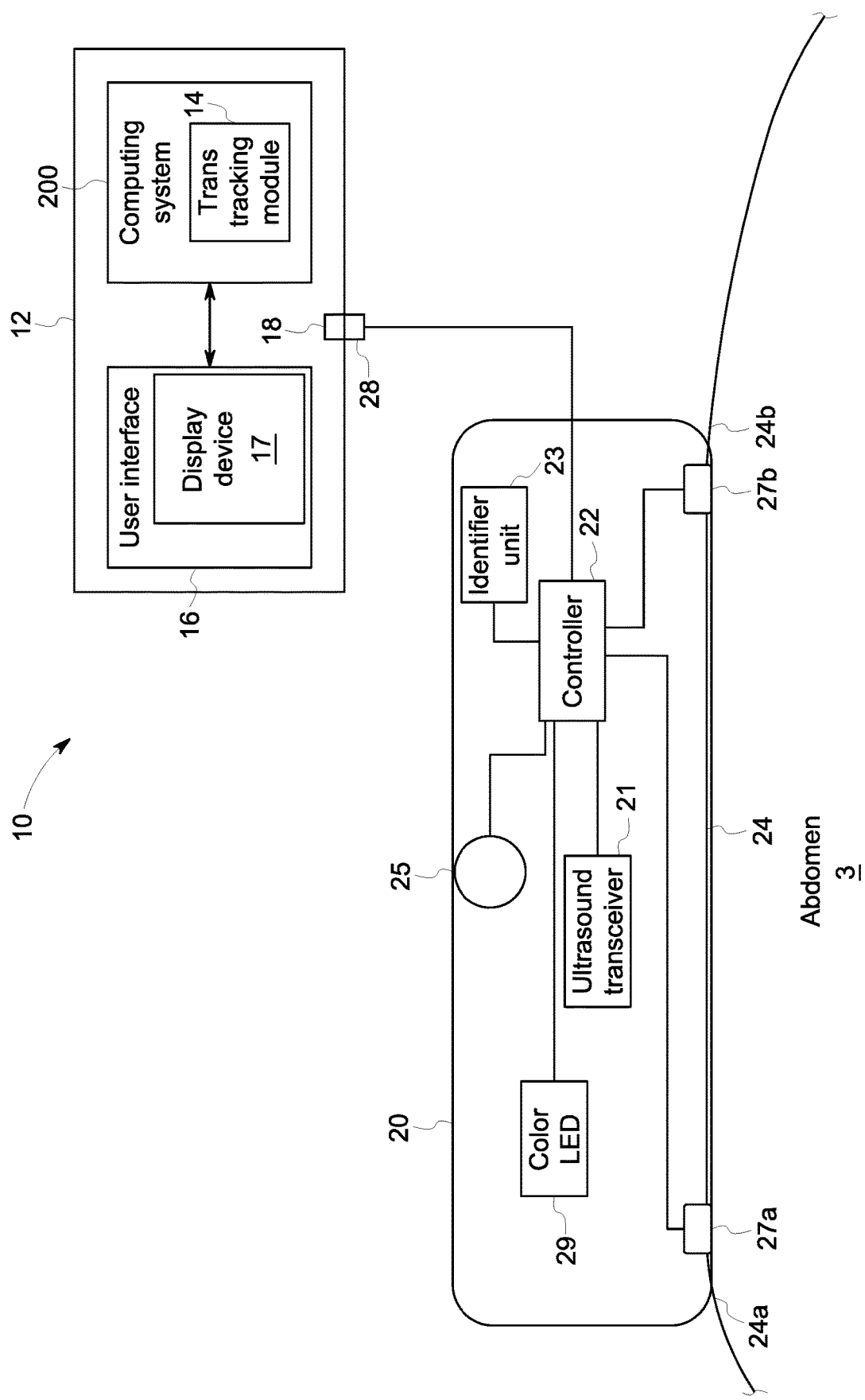
FIG. 1 is a schematic diagram depicting one embodiment of a fetal ultrasound system.
Figure 2:
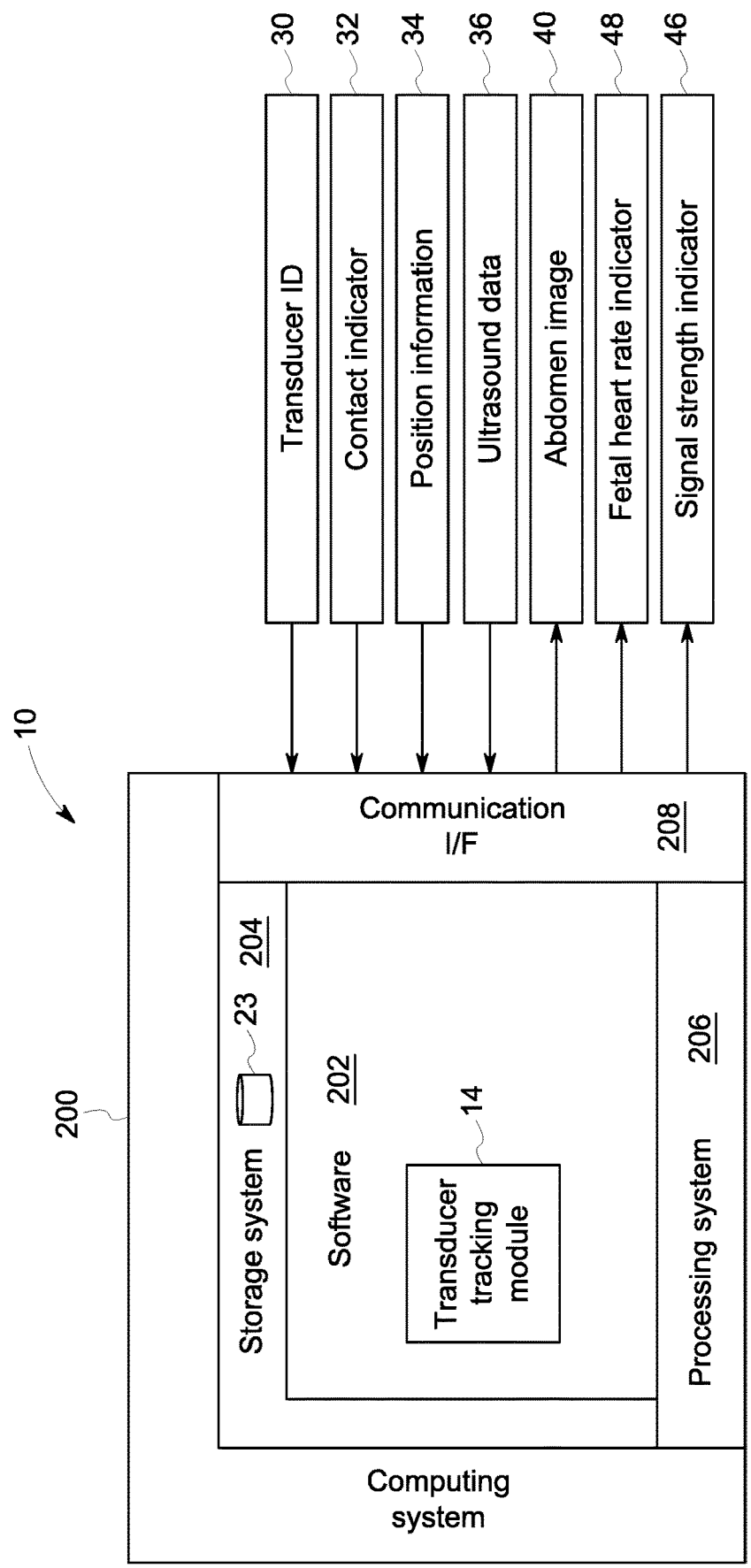
FIG. 2 is a schematic diagram of an exemplary computing system in a fetal ultrasound system.

FIGS. 1 and 2 depict one embodiment of a fetal ultrasound system 10 including a fetal ultrasound transducer 20 connected to a mother's abdomen 3 for monitoring fetal heart rate. Although FIG. 1 shows only one fetal ultrasound transducer 20, it should be understood that the fetal ultrasound system 10 may include any number of one or more fetal ultrasound transducers 20, each having the elements depicted and described with respect to FIG. 1. Each fetal ultrasound transducer 20 includes an ultrasound device 21, such as an ultrasound transceiver configured to generate waves in the ultrasonic range, to sense reflected sound waves and generate corresponding electrical signals that comprise ultrasound data for detection of fetal heartbeat. To provide just one exemplary embodiment, the ultrasound device 21 may be a single piezoelectric transceiver comprised of a number of piezoelectric crystals distributed across the device. In other embodiments, the ultrasound device 21 may comprise separate ultrasound transmitters and receivers, each being a separate set of piezoelectric crystals.

The fetal ultrasound transducer further includes one or more contact sensors 27 configured to sense contact with patient's skin and generate a contact indicator 32 based thereon. For example, the contact sensor 27 may comprise one or more capacitive sensors 27a, 27b positioned at opposing ends of the contact surface 24 of the ultrasound transducer 20. In such an embodiment, the contact indicator 32 includes a capacitance measured by each of the respective capacitive contact sensors 27a, 27b, and determines that the fetal ultrasound transducer 20 is connected to the mother's abdomen 3 when less than a threshold capacitance is detected by both capacitive sensors 27a, 27b.

The fetal ultrasound transducer 20 is configured to connect to a monitor 12. In the depicted embodiment, the transducer physically connects to the monitor 12 by connecting transducer plug 28 of the fetal ultrasound transducer 20 to a transducer receiver 18 in the monitor 12. In embodiments containing more than one fetal ultrasound transducer 20, each fetal ultrasound transducer 20 may have a separate transducer plug 28 that is received by or mates with a separate transducer receiver 18 in the monitor 12. In other embodiments, communication between the fetal ultrasound transducer 20 and the monitor 12 may be via wireless means, such as via any known wireless communication protocol. In such an embodiment, the fetal ultrasound transducer 20 may further comprise a wireless receiver/transmitter that communicates with a receiver/transmitter in the monitor 12. In such an embodiment, the monitor may comprise a separate receiver/transmitter for each fetal ultrasound transducer 20, or a receiver/transmitter that communicates with all ultrasound transducers 20 wirelessly communicating with the monitor 12.

The ultrasound transducer 20 further includes a transducer identifier unit 23 that communicates a transducer ID 30 to the monitor 12. The transducer identifier unit 23 may be, for example, a set of information stored and accessible at a certain location in the non-volatile memory of each transducer 20. In other embodiments, the identifier unit 23 may be a separate device, such as an ID chip, that provides the transducer ID 30 by either wireless or wired means. In certain examples, the transducer ID 30 comprises a vendor ID, a product ID, and a unique serial number generated and programmed into the device by the manufacturer. The product ID may, for example, contain information regarding the colored LED 29 contained in the particular transducer 20. Such information may be provided to the monitor 12 by any communication means and/or protocol, such as via a USB interface with the monitor 12.

The monitor 12 receives the ultrasound data 36, the contact indicator 32, and the transducer ID 30 from the one or more ultrasound transducers 20 connected thereto (e.g., by either wired or wireless means). The monitor 12 includes software comprising a transducer tracking module 14 executable on a processor to track the respective ultrasound transducers 20. The transducer tracking module 14 may execute steps to generate a transducer label 41, 42, 43 for each ultrasound transducer 20, and associate the transducer ID 30 with a respective transducer label 41, 42, 43, as explained in more detail below. The transducer tracking module 14 further identifies a position of each of the one or more fetal ultrasound transducers 20 connected to the monitor 12, and associates the respective transducer ID and transducer label 41, 42, 43 therewith. The transducer tracking module 14 generates an abdomen image 40 with the transducer labels 41, 42, 43 positioned thereon to visually represent the placement of the ultrasound transducers 20 on the patient's abdomen.

The monitor 12 includes or is associated with a display device 17 comprising part of a user interface system 16 including a display device 17 configured to display the abdomen image 40 with the transducer label 41, 42, 43 for each of the one or more fetal ultrasound transducers 20a, 20b, 20c. The display device 17 is also configured to display a fetal heart rate indicator 48 in association with the respective transducer label 41, 42, 43 for that fetal ultrasound transducer 20. In the depicted embodiment, the display device 17 is a touch screen display allowing user input as interaction with the user interface display 38. The display device 17 may include any type of touch screen interface layered on top of the electronic visual display of the display device 17, such as a capacitive touch screen panel, a resistive touch screen panel, or other touch screen technology.

In certain embodiments, each ultrasound transducer 20 may include an illuminable device 29, such as a colored LED 29. In certain examples, each ultrasound transducer 20 attached to the monitor 12 displays a different color light than the other transducers attached to the same monitor 12. In other embodiments, the illumination device 29 may comprise of a different type of illuminable device or may comprise multiple colored LEDs that are selectively illuminable by the controller 22 within the respective fetal ultrasound transducer 20. For example, the illumination device 29 may be illuminable in at least two different colors, and the controller 22 may be configured to control the illumination device to select one of the at least two different colors based on the transducer label 41, 42, 43 assigned thereto. To provide just one example, the illumination device 29 may comprise multiple different colored LEDs, one of which may be selected and illuminated to correspond with the transducer label 41, 42, 43 assigned by the transducer tracking module 14 to that particular fetal ultrasound transducer 20. Thereby, the illumination device 29 may be illuminated in a color to correspond to the color for the respective ultrasound transducer provided on the user interface display 38. Thereby, each respective fetal ultrasound transducer is visually associable with the abdomen image 40 and the transducer labels 41, 42, 43 provided thereon.

In certain embodiments, each of the one or more fetal ultrasound transducers 20 may comprise a position sensor 25 configured to measure position information 34 of that fetal ultrasound transducer within a two-dimensional plane or a three-dimensional space. Thereby, the position of each of the fetal ultrasound transducers is automatically determined based on the position information 34 measured by the position sensor 25. In one exemplary embodiment, the position sensor 25 may be an electromagnetic transmitter/receiver in each transducer 20a, 20b, 20c that communicate to determine a relative location among the transducers 20a, 20b, 20c. To provide just one example, each position sensor 25 may include an ultrasonic transmitter/receiver that selectively transmits and receives ultrasonic pulses to the position sensor(s) in other transducers 20b, 20c. Alternatively or additionally, the position sensors 25 may include an inertial measurement unit (IMU) containing a triad of gyroscopes and triad of accelerometers and measuring linear and angular motion. Accordingly, the position information 34 may include IMU data providing position information in three-dimensional space, and relative position information consisting of two-dimensional distance information describing position relative to one or more other of the ultrasound transducers.

In other examples, the position sensor 25 may be an IR-based optical sensor embedded within each transducer 20. Each infrared (IR) position sensor 25 transmits and receives IR data. Based on the reflective intensity measured using the optical fibers of each position sensor 25, the distance(s) between the transducers can be determined and communicated to the monitor 12, such as through the aforementioned USB interface.

In certain embodiments, the fetal ultrasound transducer 20 may further include a controller 22 that communicates with the various devices and systems within the ultrasound transducer 20, including the ultrasound transceiver 21, the identifier unit 23, the contact sensor(s) 27, and/or the position sensor 25. The controller 22 may control communication between the respective elements and the monitor 12, such as to receive the ultrasound data 36 from the ultrasound transceiver 21, the transducer ID 30 from the transducer identifier unit 23, and/or the contact indicator 32 from the contact sensor(s) 27, and facilitate communication of those values to the monitor 12. Similarly, the controller 22 may function to provide control signals to the respective elements 21, 23, 25, 27, 29 based on control instructions provided by the monitor 12, such as generated by the transducer tracking module 14.

In certain embodiments, the controller 22 may also provide power distribution and control function, receiving power from a power source and distributing it to the various elements 21, 23, 25, 27, 29 according to the needs of the fetal ultrasound system 10. In embodiments where the fetal ultrasound transducer 20 physically connects to the monitor 12, the monitor 12 may be the power source for the fetal ultrasound transducer 20, and thus power may be provided from the monitor 12 through the transducer plug 28 and cord to the fetal ultrasound transducer 20. In other embodiments where the fetal ultrasound transducer 20 is a wireless device, a battery may be connected thereto, and power from the battery controlled and distributed by the controller 22.

FIGS. 3-8 depict various embodiments of a user interface display 38 provided on a display device 17 and generated by the user interface system 16. The user interface display 38 generally provides an abdomen image 40 and a transducer label 41, 42, 43 associated with each of the one or more ultrasound transducers 20. In certain embodiments, a first step may be performed via the user interface display 38 to select the number of fetuses for which heart rate monitoring will occur, such as a single fetus, twins, triplets, etc. For example, the user interface display 38 may be configured to provide an initial screen allowing a user to select a number of fetuses. The user interface display may then automatically display a corresponding number of active transducer indicator locations 45 and parameter blocks 47. In other embodiments, the user interface system 16 may be configured to automatically display a number of active transducer indicator locations 45 and/or parameter blocks 47 based on a number of fetal ultrasound transducers 20 connected to the monitor 12. For example, the transducer tracking module 14 may be configured to automatically detect when a transducer plug 28 of a fetal ultrasound transducer 20 is connected to respective transducer receiver 18 in the monitor 12, and to adjust the user interface display 38 to provide the active transducer indicator location 45 and parameter block 47 accordingly. In still other embodiments, a default number of active transducer indicator locations 45 and parameter blocks 47 may be provided and may remain blank until a fetal ultrasound transducer 20 is connected to the monitor 12 and provides information to be displayed.

Figure 3:
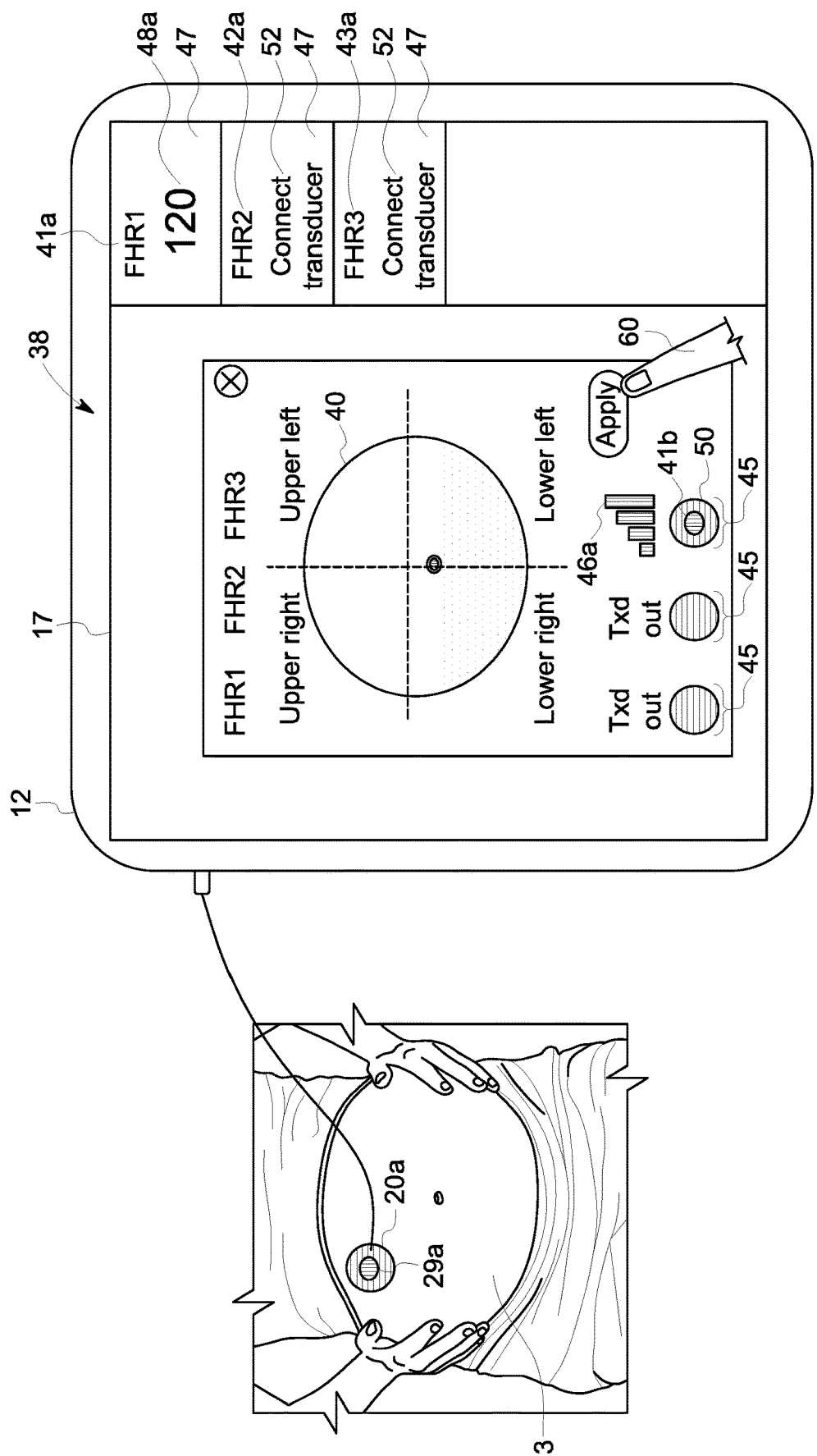
FIGS. 3-8 depict exemplary embodiments of a user interface for a fetal ultrasound system, and corresponding methods of conducting fetal ultrasound monitoring.

In the example of FIG. 3, one fetal ultrasound transducer 20*a* is positioned on the mother's abdomen 3 and is connected to the monitor 12. Accordingly, one active transducer indicator location 45 and a first parameter block 47 display a first transducer label 41 associated with that fetal ultrasound transducer 20. The transducer label 41 may be any type of visual label that identifies the respective fetal ultrasound transducer 20*a*. In the depicted embodiment, the first transducer label 41 includes an alphanumeric label 41*a* identifying "FHR1" indicating the device and physiological parameters are associated with a first fetus. The first transducer label 41 may also include a color indicator 41*b*, which may be an alternative or in addition to the alphanumeric label 41*a*. The color label 41*b* indicates a color associated with the respective transducer 20*a*, which may be provided at numerous locations on the user interface display 38, such as on a transducer icon 50 and/or indicating the respective physiological parameters and aspects of the user interface display 38 associated with the first fetus and the first fetal ultrasound transducer 20*a*.

The user interface display 38 may further provide a signal strength indicator 46 to indicate the signal strength of the heartbeat measurement by the fetal ultrasound transducer 20. This is a visual indication of the strength of the heartbeat measurement and can be used by a clinician to optimally place the respective fetal ultrasound transducer 20 on the mother's abdomen 3. For example, the clinician placing the ultrasound transducer 20 may move the transducer 20 based on the signal strength indicator 46 in order to select an optimal location for measuring the respective fetus' heartbeat. In the depicted embodiment, the signal strength indicator for the first ultrasound transducer 20*a* is provided in the associated active transducer location 45, and is provided in a color that corresponds with the first transducer label 41*b*. Namely, the signal strength indicator 46*a* is provided in red, the same color as the first transducer label 41*b*, providing an additional visual indication of the fetal ultrasound transducer 20*a* to which the signal strength indicator 46*a* belongs.

Providing additional visual association between the fetal ultrasound transducer 20*a* and associated parts of the user interface display 38, the fetal ultrasound transducer 20*a* may comprise a light source 29, such as a colored LED, that illuminates in the same color as the respective transducer label 41*b*. In the embodiment depicted in FIG. 3, the first fetal ultrasound transducer 20*a* has red illumination source 29, such as a red LED, that corresponds with the red color of the first transducer label 41*b*.

In certain embodiments, the transducer tracking module 14 automatically determines the fetal heart rate and displays a corresponding fetal heart rate indicator 48 upon detecting that a respective fetal ultrasound transducer 20 is connected to a mother's abdomen 3 and connected to the monitor 12. For example, upon detecting less than a threshold capacitance from the capacitive contact sensors 27*a*, 27*b*, the fetal ultrasound system 10 may be configured to automatically measure and display fetal heart rate determined based on ultrasound data 36 gathered by the respective ultrasound transducer 20. In such an embodiment, the fetal heart rate indicator 48 may be automatically displayed in association with respective transducer label, including the alphanumeric transducer label 41*a* and/or the color transducer label 41*b*. In other embodiments, the transducer tracking module 14 may be configured to determine and display the fetal heart rate upon input from a user instructing such determination and/or acknowledging placement of the respective fetal ultrasound transducer 20. For example, referencing FIG. 3, the clinician may provide input via the user interface display 38 once the respective fetal ultrasound transducer 20*a* has been placed, such as based on guidance provided by the signal strength indicator 46*a*. In the example of FIG. 3, such input by a user 60 is provided by selecting the "apply" button on the touch screen display device 17.

The transducer tracking module 14 is further executed to associate the transducer ID 30 for the respective ultrasound transducer 20*a*, 20*b*, 20*c* with each transducer label 41, 42, 43 for that respective device. Thereby, the respective fetal heartbeat recordings and/or fetal heart rate indicators can be associated with a particular ultrasound transducer 20*a*, 20*b*, 20*c*. That particular transducer 20*a*, 20*b*, 20*c* is associated with a location on the mother's abdomen 3. Thus, in the case of multiples, the ultrasound transducer 20*a*, 20*b*, 20*c* is associated with a particular fetus.

A position of each of the one or more ultrasound transducers 20*a*, 20*b*, 20*c* connected to the monitor 12 is identified by the transducer tracking module 14. Such position identification may be based on user input provided at the user interface display 38, or may be determined automatically by the system 10. The abdomen image 40 is then adjusted to provide transducer icons 50 with respective transducer labels 41, 42, 43 positioned thereon based on the position of each of the one or more fetal ultrasound transducers 20*a*, 20*b*, 20*c*.

Figure 4:
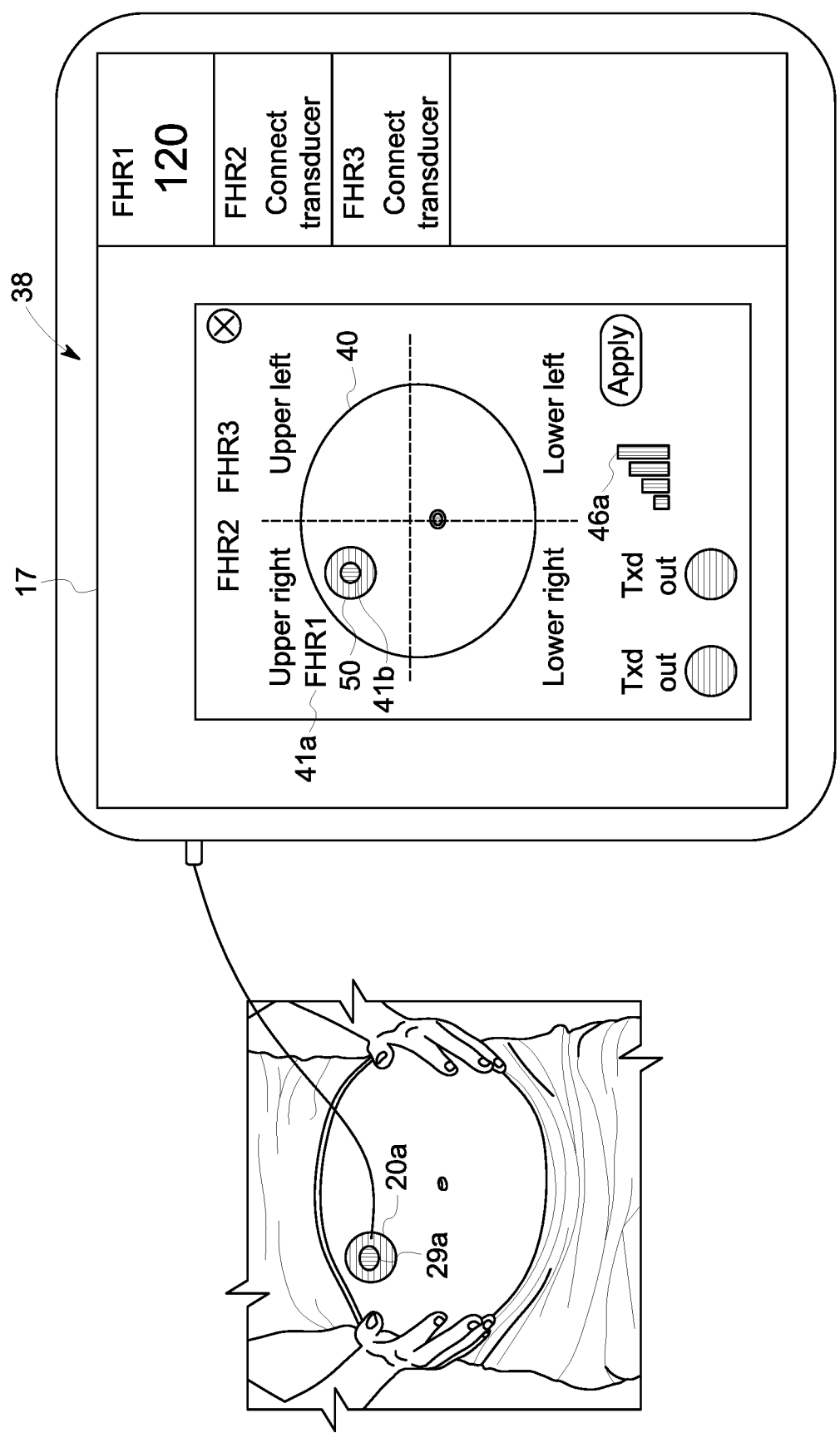
Figure 5:
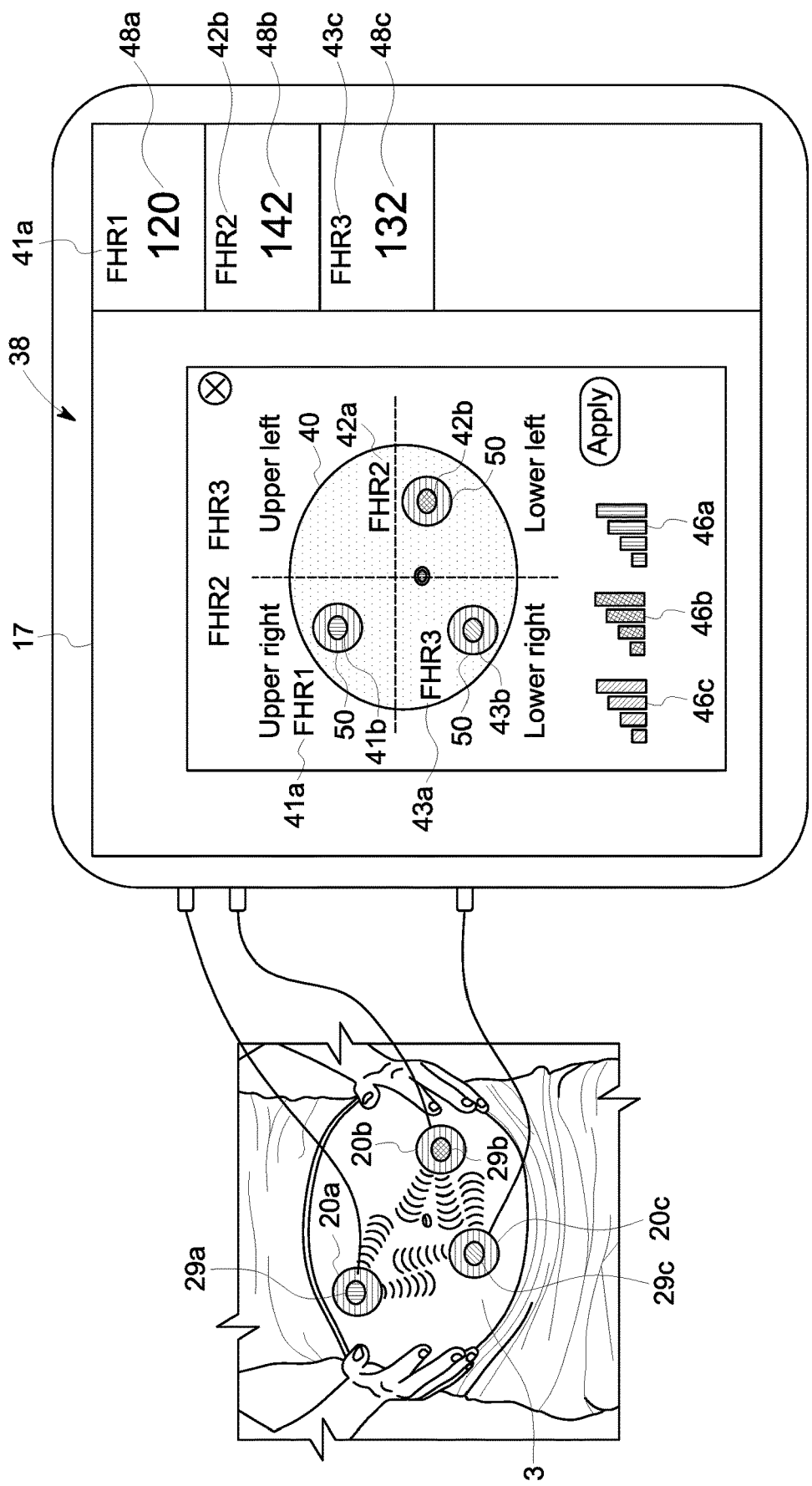

FIG. 4 provides an exemplary embodiment showing the first transducer label 41 positioned on the abdomen image 40 to correspond with the position of the first ultrasound transducer 20*a* on the mother's abdomen 3. As additional fetal ultrasound transducers 20*b*, 20*c* are attached to the mother's abdomen 3, such fetal ultrasound transducers are added to the abdomen image 40. FIG. 5 provides one example where three fetal ultrasound transducers 20*a*, 20*b*, and 20*c* are connected to the mother's abdomen 3 and represented accordingly as transducer icons 50 on the abdomen image 40, differentiated by the respective transducer labels 41, 42, 43 positioned thereon. As shown, the alphanumeric transducer labels 41*a*, 42*a*, 43*a* are displayed next to the circular image representing each ultrasound transducer 20*a*, 20*b*, 20*c*. Similarly, a color transducer label 41*b*, 42*b*, 43*b* is provided within each circular transducer icon 50, the color of which corresponds to the colored illumination source 29 of the respective ultrasound transducer 20*a*, 20*b*, 20*c*. In the example, each of the ultrasound transducers 20*a*, 20*b*, 20*c* has an illumination device 29 being a colored LED 29*a* (red), 29*b* (orange), and 29*c* (green). Correspondingly, everything associated with the first ultrasound transducer 20*a* is provided in red (transducer label 41*b*), everything associated with the second ultrasound transducer 20*b* is provided in orange (transducer label 42*b*), and everything associated with the third ultrasound transducer 20*c* is provided in green (transducer label 43*b*). In certain embodiments, the color of the respective illumination device 29*a*, 29*b*, 29*c* may be provided as part of the transducer ID 30, and the color transducer labels 41*b*, 42*b*, 43*b* may be assigned accordingly.

In embodiments where the ultrasound transducers 20*a*, 20*b*, 20*c* have position sensors therein, the transducer positions may be automatically determined, and the corresponding abdomen image 40 may be generated automatically based on the position information 34 measured by each position sensor 25. Namely, the transducer tracking module 14 may automatically generate an abdomen image 40 having transducer icons 50 showing the location of each transducer 20 and labeled accordingly. For example, the three transducers 20 shown in FIG. 5 may each comprise a position sensor 25 having an IMU and electromagnetic receiver/transmitter that communicates with the various other sensors (e.g. via ultrasound) to determine a relative location. The abdomen image 40 may be automatically generated based on such information. Further, the abdomen image 40 may be automatically updated if on one of the transducers 20*a*, 20*b*, 20*c* is repositioned, for example. Thereby, the relative movements of the ultrasound transducers 20*a*, 20*b*, 20*c* can be tracked and visualized on the user interface display 38.

Figure 6:
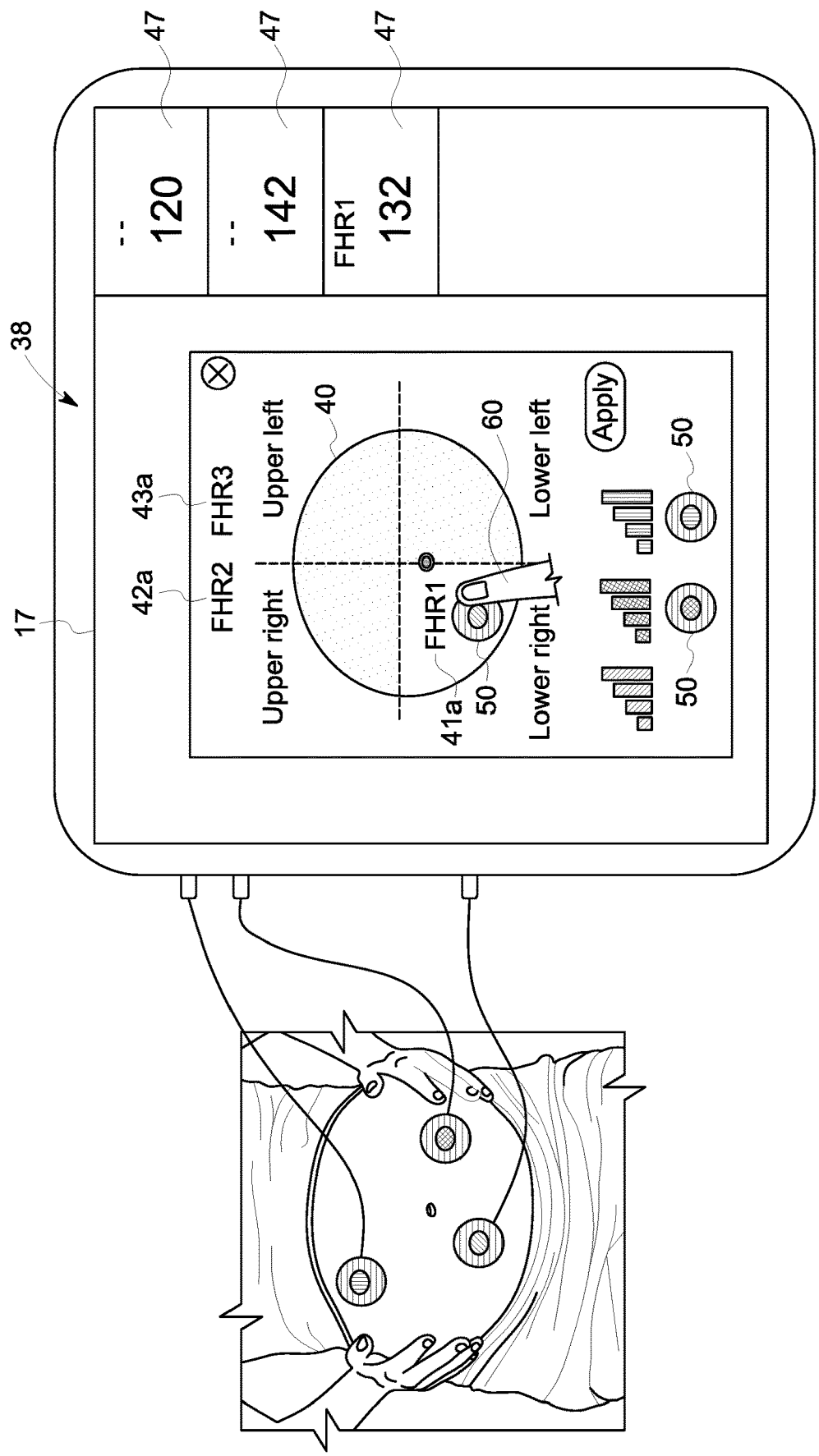

In other embodiments, the position of each ultrasound transducer may be identified based on user input. FIG. 6 provides one example of how such user input may be provided via the user interface display 38. In the example embodiment, user input regarding transducer position is provided by placing each transducer icon 50 onto the abdomen image 40. For example, the user interface display 38 may be designed to facilitate such user input by allowing the user 60 to select each transducer icon 50 and place it on the abdomen image 40. In the depicted example, the user interface display 38 is a touch screen configured to receive touch input by the user 60 to place the transducer icons 50, as shown. In certain embodiments, the user interface display 38 may be further arranged to allow the user to associate the transducer labels 41, 42, 43 with each transducer icon 50 indicating the respective position on the abdomen image, and thereby with each corresponding transducer ID 30. For example, the user interface display 38 may be configured to allow a user 60 to select each transducer label, such as by touching the label on the screen, and placing each label next to a corresponding transducer icon 50 (e.g. placed on the abdomen image 40 by the clinician). In certain embodiments, once all transducer labels are associated with respective transducer icons, the user may hit apply, at which point the transducer ID 30 for each respective ultrasound transducer 20*a*, 20*b*, 20*c* may be associated with each of the transducer labels 41, 42, 43.

In various fetal ultrasound system 10 configurations and embodiments, the transducer labels 41, 42, 43 may be automatically assigned by the transducer tracking module 14, or may be assigned based on user input. In certain embodiments described herein, the alphanumeric transducer labels 41*a*, 42*a*, 43*a* may be assigned separately from the color transducer labels 41*b*, 42*b*, 43*b*. For example, the color transducer labels 41*b*, 42*b*, 43*b* may be automatically assigned, such as based on information transmitted as part of the transducer ID 30; while the alphanumeric transducer labels 41*a*, 42*a*, 43*a* may be manually assigned. In other embodiments, all alphanumeric transducer labels 41*a*, 42*a*, 43*a* and color transducer labels 41*b*, 42*b*, 43*b* may be manually assigned or automatically assigned (which, in embodiments with position sensors 25, may account for the sensed position of the transducer).

For automatic assignment, the transducer tracking module 14 may assign the transducer labels according to an order of connection of the fetal ultrasound transducers 20 to the monitor 12. For example, the first fetal ultrasound transducer 20*a* to be connected to the monitor 12 may be assigned the first transducer label 41, the second fetal transducer 20*b* to be connected to the monitor 12 may be assigned the second transducer label 42, and the third fetal ultrasound transducer 20*c* connected to the monitor 12 may be assigned the third transducer label 43. The fetal heart rate indicator 48 and/or heartbeat traces, and the transducer icon 50 may then be automatically displayed accordingly on the user interface display 38, such as exemplified in FIGS. 3-8.

In certain embodiments, the transducer tracking module 14 may provide an initial transducer label 41, 42, 43, such as based on the order of connection to the monitor 12, which may then be later adjusted during the monitoring and data presentation process. For example, the transducer tracking module 14 may automatically adjust the assigned transducer labels 41, 42, 43 based on sensed position as additional transducers 20 are connected, such as according to the logic described below. Alternatively or additionally, the user interface display 38 may be configured to facilitate and receive user input to adjust the transducer labels 41*a*, 41*b*, 42*a*, 42*b*, 43*a*, 43*b*, such as by the touch input procedures described above with respect to FIG. 6. Accordingly, by either automatic or manual procedures, some or all of the transducer labels 41*a*, 41*b*, 42*a*, 42*b*, 43*a*, 43*b* may be reorganized, reassigned, and represented, such as exemplified in FIGS. 6-7.

One commonly preferred way of organizing the fetal heart rate information is to assign them from lowest to highest. Namely, the lowest positioned fetus (i.e., that positioned closest to the cervix) is designated the first fetus, the second highest fetus designated as second, and so on. Accordingly, the transducer tracking module 14 may utilize the position information 34 provided by the position sensors 25 to assign the transducer labels 41*a*, 41*b*, 42*a*, 42*b*, 43*a*, 43*b* and/or to reorganize the transducer label assignment as additional fetal ultrasound transducers 20 are connected to the mother's abdomen 3 and to the monitor 12. Thus, the transducer tracking module 14 may determine the lowest positioned fetal ultrasound transducer 20 on the mother's abdomen 3 based on the position information 34 describing the position of the ultrasound transducer 20*a*, 20*b*, 20*c* within the two-dimensional plane.

Figure 7:
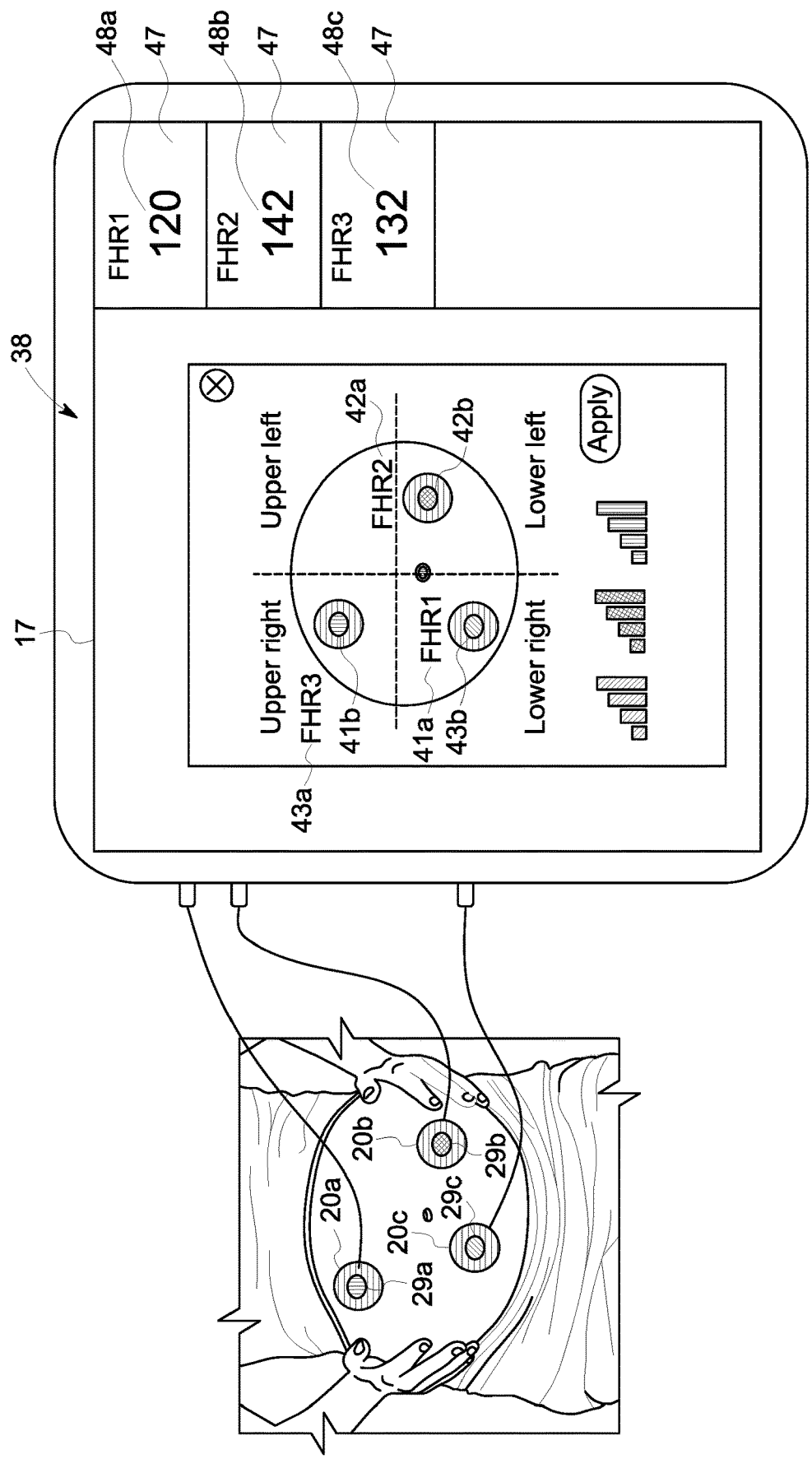

Upon such assignment, or reassignment, the transducer IDs 30 for each of the fetal ultrasound transducers 20 *a*, 20 *b*, 20 *c* are assigned or associated with the respective transducer labels 41, 42, 43 accordingly. In certain embodiments, the alphanumeric transducer labels 41*a*, 42*a*, 43*a* may be reorganized and/or reassigned upon connection of all of the fetal ultrasound transducers 20*a*, 20*b*, 20*c*, but the originally-assigned transducer labels 41*b*, 42*b*, 43*b* may remain the same. With reference to FIG. 7, for example, the assignment of the alphanumeric transducer labels 41*a*, 42*a*, 43*a* are reorganized to swap the original assignment of the first alphanumeric transducer label 41*a* and the third alphanumeric transducer label 43*a* according to the position of the respective fetal ultrasound transducers 20*c* and 20*c*. However, the color transducer labels 41*b* and 43*b* remain the same, which continue to match the colored LEDs 29*a* and 29*c* on the respective fetal ultrasound transducers 20*a* and 20*c*. Thus, the lowest positioned fetal ultrasound transducer 20*a*, 20*b*, 20*c* may be assigned the first alpha numeric transducer label 41*a*. The next lowest fetal ultrasound transducer 20*a*, 20*b*, 20*c* with respect to the two dimensional plane may then be identified and assigned the second alphanumeric transducer label 42*a*, and so on. Such change may be made, for example, once all of the fetal ultrasound transducers are connected, such as upon receipt of user input indicating that the position of all devices has been finalized. The parameter blocks 47 presenting the fetal heart rate indicators 48 may also be reorganized accordingly, such as to present the first fetal heart rate indicator 48*a* ("FHR1") at the highest location and the third fetal heart rate indicator 48*c* ("FHR3") in the lowest location.

In other embodiments, such assignment of the transducer labels 41, 42, 43 may be manually provided by the user via the user interface display 38, such as by touching and dragging the respective alphanumeric transducers labels 41*a*, 42*a*, 43*a* and the color transducer labels 41*b*, 42*b*, 43*b* and placing them in a position adjacent to the transducer icon 50 for the respective fetal ultrasound transducer 20*a*, 20*b*, 20*c*.

Figure 8:
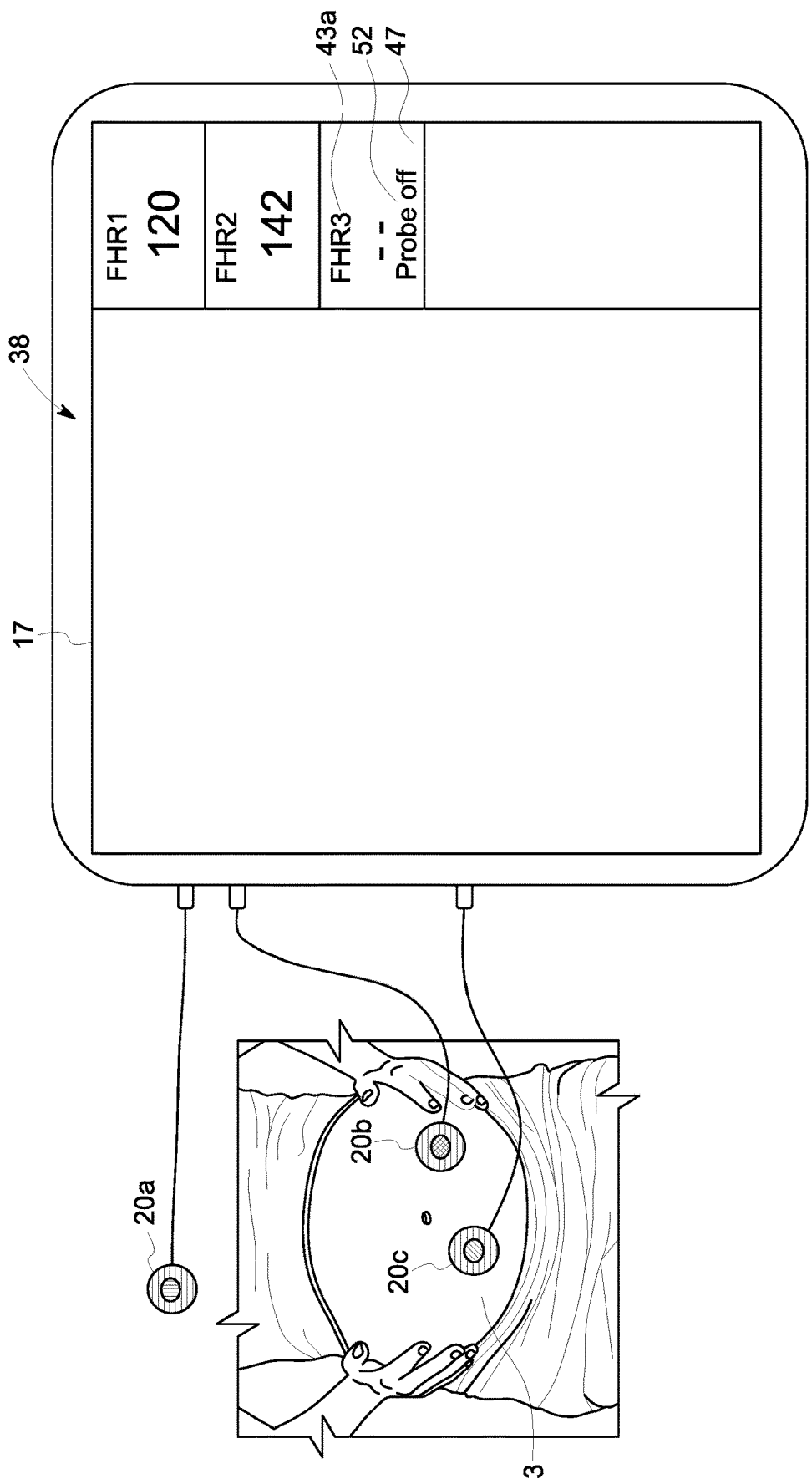

In certain embodiments, the transducer tracking module 14 may be configured to operate the user interface display 38 to provide certain status alerts 52 to an operator. Referring to FIG. 8, for example, the transducer tracking module 14 may be configured to provide a "probe off" status alert 52 in connection with a transducer label 41, 42, 43 when an associated fetal ultrasound transducer 20*a*, 20*b*, 20*c* has been removed or has fallen off the mother's abdomen 3. For example, if the one or more capacitive sensors 27*a*, 27*b* detect less than the threshold capacitance, then the "probe off" status alert 52 may be provided for that transducer on the user interface display 38. In the example of FIG. 8, the fetal ultrasound transducer 20A associated with the third alphanumeric transducer label 43*a* (FIG. 7) is disconnected from the mother's abdomen 3. Accordingly, no fetal heart rate indicator 48 is provided in the corresponding parameter block 47, and instead a "probe off" status alert 52 is displayed. In certain examples the abdomen image may be adjusted to reflect the missing transducer. Another example is shown at FIG. 3, where the status alert 52 indicates that no ultrasound transducer is connected to the monitor 12 in association with a respective transducer label 41*a*, 42*a*, 43*a*, 41*b*, 42*b*, 43*b*. In the example, the status alert 52 displays "connect transducer" indicating that no fetal ultrasound transducer 20 is connected to the monitor, such as at the corresponding transducer receiver 18.

Accordingly, the system and method described herein enable tracking of fetal ultrasound transducers 20*a*, 20*b*, 20*c* so that the transducers can be repositioned to measure heart rate from the same fetus between monitoring sessions. For example, the user interface display 38 generated from the previous session can be displayed in order to instruct a clinician on where and how to connect the respective ultrasound transducers 20*a*, 20*b*, 20*c*—e.g. starting with the previously-applied configuration.

Furthermore, if the clinician were to misplace, or swap one or more of the fetal ultrasound transducers, then the system may automatically detect such an error. In that event, the system may generate an alert to a clinician regarding the misplacement. Alternatively or additionally, in situations where the placement of two fetal ultrasound transducers 20*a*, 20*b*, 20*c* are swapped in position, the transducer tracking module 14 may be configured to automatically compensate for the swap, and reassign the transducer labels 41*a*, 42*a*, 43*a*, 41*b*, 42*b*, 43*b* accordingly. Moreover, the transducer tracking module 14 may be configured to automatically associate and correlate the previously measured fetal heart rate data correctly with the newly, gathered fetal heart rate data, accounting for the detected transducer swap.

FIG. 2 is a schematic diagram of an exemplary computing system 200 in a fetal ultrasound monitor 12. The computing system 200 includes a processing system 206, storage system 204, software 202, and communication interface 208. The processing system 206 loads and executes software 202 from the storage system 204, including the transducer tracking module 14, which is an application within the software 202. The transducer tracking module 14 includes computer-readable instructions that, when executed, direct the processing system 206 to operate as described in herein in further detail, including to execute the steps to identify the position of each fetal ultrasound transducer 20 and to provide an abdomen image 40 having transducer icons and/or labels located thereon depicted said transducer positions.

Although the computing system 200 as depicted in FIG. 2 includes one software 202 encapsulating one transducer tracking module 14, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes a processor, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device, but can also be distributed across multiple processing devices or sub-systems that cooperate in executing program instructions.

The storage system 204 may comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as with the controller 22 of each ultrasound transducer and/or a controller for the user interface system 16 and/or display device 17. In certain embodiments, the communication interface 208 may also be configured to receive information transmitted from the position sensors 25 in each ultrasound transducer 20, which may have a separate transmission/receipt means (e.g. wireless) than the ultrasound data 36, contact indicator 32, transducer ID 30, etc.

Figure 9:
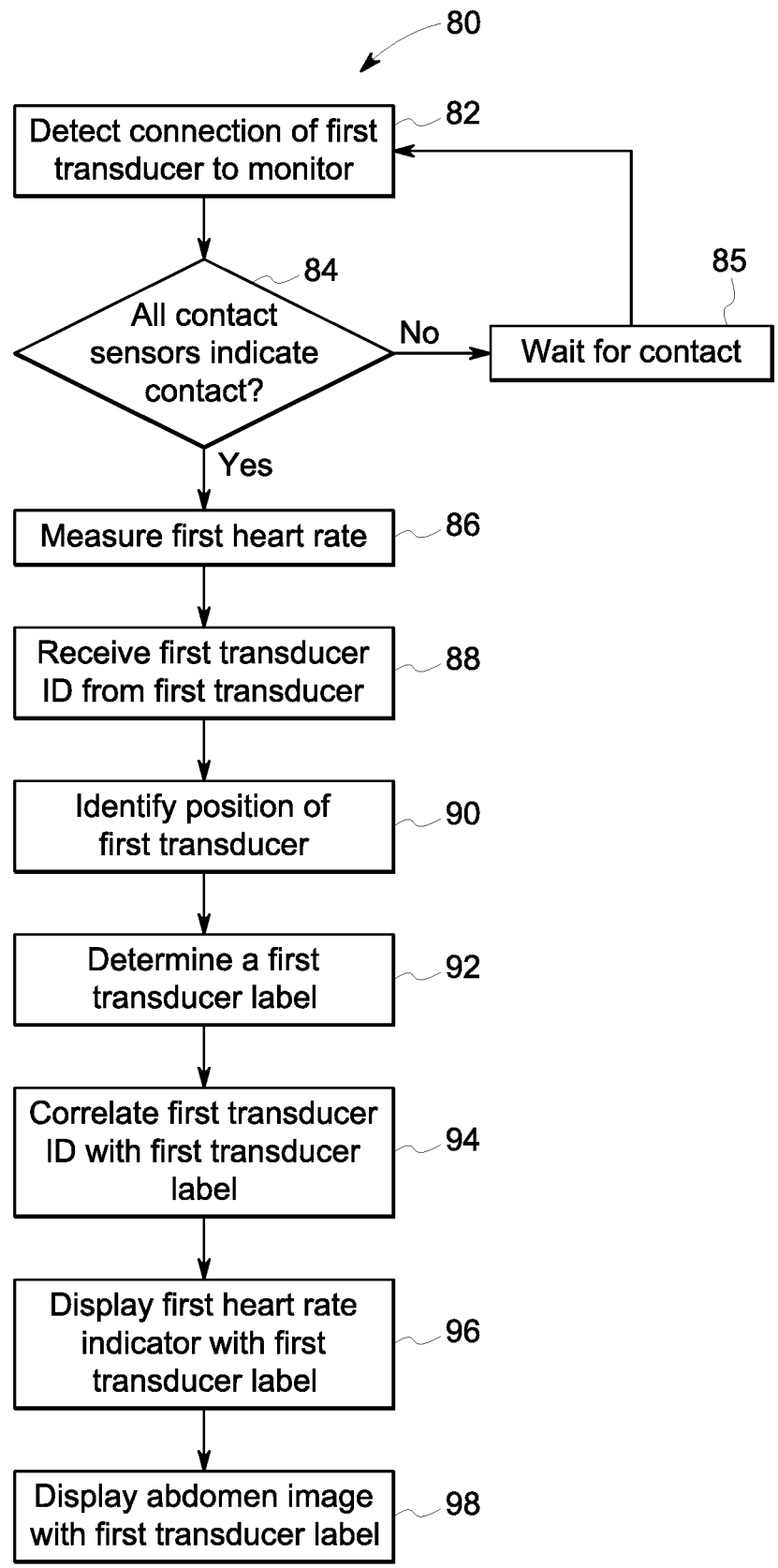
FIGS. 9-10 depict exemplary methods, or portions thereof, of fetal ultrasound monitoring.
Figure 10:
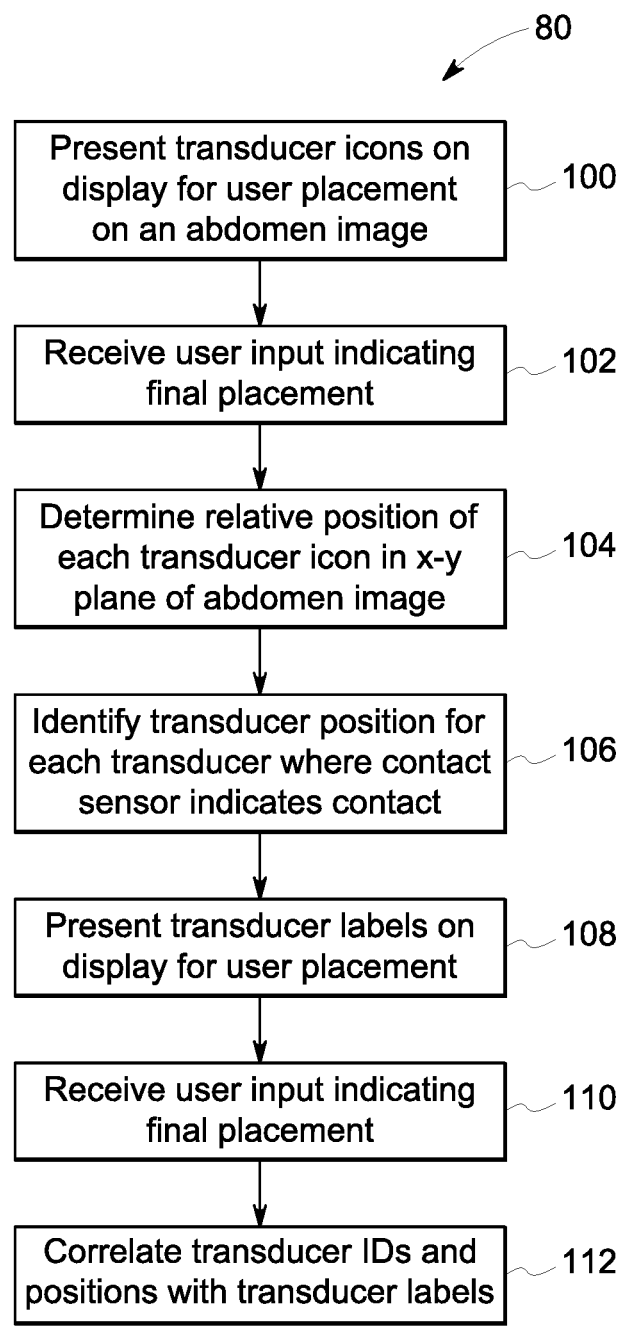

FIGS. 9-11 depict various embodiments of the method 80 of fetal ultrasound monitoring, or portions of said method. FIG. 9 provides a flowchart of one embodiment of a method 80 of fetal ultrasound monitoring that begins upon detection of a first ultrasound transducer 20*a* to a monitor 12 (step 82). Instructions are executed at step 84 to determine whether all contact sensors indicate that the first ultrasound transducer 20*a* is contacting the patient's abdomen based on the contact indicator 32 supplied by the one or more contact sensors therein. If the contact sensors do not indicate contact, then the system waits for indication of contact, repeating steps 85 and 82, and no further assessment is made. Once contact is indicated at step 84, a first heart rate is measured at step 86 based on ultrasound data 36 gathered by the first ultrasound transducer 20*a*. Step 88 is then executed to receive a first transducer ID from the first transducer, such as from the identifier unit 23 within the first ultrasound transducer 20*a*, as described above. The system also identifies a position of the first transducer 20*a* at step 90, such as based on user input as exemplified herein or by automatic position determination via input from a position sensor 25 in the respective fetal ultrasound transducer 20*a*. A first transducer label 41*a*, 41*b* is then determined at step 92, which may be based on the position of the first transducer identified at step 90. A first transducer ID 30 is correlated with the first transducer label at step 94, and a first heart rate indicator is displayed in correlation with the first transducer label at step 96. An abdomen image is displayed at step 98 with the transducer icon 50 located thereon at a location that corresponds with the position of the first transducer 20*a* on the mother's abdomen 3, and first transducer label 41*a*, 41*b* provided therewith.

In certain embodiments, the system 10 may be further configured to control an illumination device 29 based on the first transducer label 41. For example, in an embodiment where the illumination device 29 is illuminable in at least two different colors, the system, such as executing the instructions stored as part of the transducer tracking module 14, may select one of the at least two different illumination colors to correspond with the first transducer label 41, and may control illumination of the illumination device 29 based thereon. Accordingly, the various fetal ultrasound transducers 20*a*, 20*b*, 20*c* may be interchangeable, and the system may automatically correlate the transducer with a respective fetus and fetal heart rate measurement based on the sensed position of the respective fetal ultrasound transducer 20*a*, 20*b*, 20*c*. The illumination device 29 can then be used to provide a visual indication of which fetus and fetal heart rate measurement that respective fetal ultrasound transducer 20*a*, 20*b*, 20*c* has been assigned to.

FIG. 10 depicts one embodiment of a method 80 of fetal ultrasound monitoring, and specifically method steps for providing a user interface and receiving user input to identify positions of ultrasound transducers 20 connected to a mother's abdomen. Transducer icons are presented on a user display for user placement at step 100. For example, the same number of transducer icons 50 may be presented on the display corresponding with the number of fetal ultrasound transducers 20*a*, 20*b*, 20*c* that are connected to the monitor 12 and in contact with the mother's abdomen 3. User input indicating final placement is received at step 102, such as selection of the "apply" button shown in the exemplary embodiments depicted at FIGS. 3-7. The position of each transducer icon is determined in an XY-plane (or XYZ-space, if a 3D image) based on the user placement of the transducer icons 50 on the abdomen image 40. For example, the abdomen image 40 provided on the user interface display 38 may be mapped with an XY-grid that corresponds with the sensor grid of the touch screen—e.g., the center point of each transducer icon 50 may be identified corresponding with the XY-grid of the abdomen image 40. The transducer position for each fetal ultrasound transducer 20a, 20b, 20c is then identified based on the placement of the transducer icons on the abdomen image.

In certain embodiments, the system 10, such as by executing instructions comprising the transducer tracking module 14, may then automatically determine the transducer labels 41a, 42a, 43a according to the identified position for each of the fetal ultrasound transducers 20a, 20b, 20c where the respective contact sensors 27 indicate contact with the mother's abdomen 3. For example, the lowest positioned transducer may be assigned the first alphanumeric transducer label 41a, and so on as described above.

In other embodiments, the certain or all transducer labels may be assigned based on user input. In the example of FIG. 10, the transducer labels are presented on the display at step 108 for user placement, such as a number of transducer labels corresponding with the number of fetal ultrasound transducers 20 that are connected to the monitor 12 and in contact with the mother's abdomen. Once the system receives user input at step 110 indicating final placement, the transducer labels are correlated accordingly with the transducer IDs and positions of the fetal ultrasound transducers 20 accordingly.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A method of fetal ultrasound monitoring, the method comprising:
    detecting contact of a first ultrasound transducer with a mother's abdomen based on input from a contact sensor in the first ultrasound transducer and contact of a second ultrasound transducer with the mother's abdomen based on input from a sensor in the second ultrasound transducer;
    receiving a first transducer ID from the first ultrasound transducer and a second transducer ID from the second ultrasound transducer;
    correlating the first transducer ID with a first transducer label that identifies the first ultrasound transducer;
    assigning a first color of at least two different colors to the first ultrasound transducer within a first housing;
    correlating the second transducer ID to with a second transducer label that identifies the second ultrasound transducer;
    assigning a second color of the at least two different colors, which is different than the first color, to the second ultrasound transducer within a second housing;
    measuring a first heart rate based on output of an ultrasound device in the first ultrasound transducer and a second heart rate based on output of an ultrasound device in the second ultrasound transducer;
    displaying a first heart rate indicator on a display device in association with the first transducer label and a second heart rate indicator on a display device in association with the second transducer label;
    identifying a first position of the first ultrasound transducer and a second position of the second ultrasound transducer in at least a two-dimensional plane;
    displaying the first transducer label and the second transducer label on an abdomen image based on the first position and the second position to visually represent the placement of the first ultrasound transducer and the second ultrasound transducer on the mother's abdomen; and
    illuminating a first illumination device on the first housing in the first color and illuminating a second illumination device on the second housing in the second color to simultaneously provide a visual association between the first ultrasound transducer and the first transducer label displayed on the abdomen image and the second ultrasound transducer and the second transducer label displayed on the abdomen image.

2. The method of claim 1, wherein identifying the first position includes measuring first position information of the first ultrasound transducer with a position sensor in the first ultrasound transducer, and determining the first position with respect to the at least the two dimensional plane based on at least the first position information.

3. The method of claim 2, wherein identifying the second position includes measuring second position information of the second ultrasound transducer with a position sensor in the second ultrasound transducer, and determining the second position with respect to the two dimensional plane based on at least the first position information and the second position information.

4. The method of claim 3, further comprising automatically generating the abdomen image with the first transducer label and the second transducer label positioned thereon based on the first position and the second position.

5. The method of claim 3, wherein the first transducer ID is correlated with the first transducer label based on the first position and the second transducer ID is correlated with the second transducer label based on the second position.

6. The method of claim 1, wherein the first ultrasound transducer includes at least one capacitive sensor, the method further comprising:
    detecting that a capacitance measured by the capacitive sensor is greater than a threshold capacitance; and
    generating a probe off alert in association with the first transducer label.

7. The method of claim 6, wherein detecting connection of the first ultrasound transducer to the mother's abdomen includes determining that all of the at least one capacitive sensors in the first ultrasound transducer measure less than the threshold capacitance.

8. The method of claim 1, further comprising:
    presenting, on the display device, a user interface configured to receive user input placing the first transducer label at a location on the abdomen image corresponding to a location of the first ultrasound transducer on the mother's abdomen; and
    wherein the first position is identified based on the user input.

9. The method of claim 1, wherein the first color is manually selected.

10. The method of claim 1, wherein the first color is selected based on the colors included in the at least two different colors.

11. The method of claim 1, wherein the second color is selected based on the first color and the colors included in the at least two different colors.

12. The method of claim 1, wherein displaying the first transducer label on the abdomen image comprises providing a color indicator that is the first color on the first transducer label.

13. The method of claim 1, further comprising:
providing, on the display device, a first signal strength indicator to indicate a signal strength of the first heart rate measurement by the first ultrasound transducer and a second signal strength indicator to indicate a signal strength of the second heart rate measurement by the second ultrasound transducer;
wherein the at least one of the first heart rate indicator and the first signal strength indicator is provided in the first color on the display device; and
wherein the at least one of the second heart rate indicator and the second signal strength indicator is provided in the second color on the display device.

14. The method of claim 1, further comprising:
detecting connection of a third ultrasound transducer to the mother's abdomen based on input from a sensor in the third ultrasound transducer;
receiving a third transducer ID from the third ultrasound transducer;
correlating the third transducer ID with a third transducer label that identifies the third ultrasound transducer;
assigning a third color of the at least two different colors, which is different than the first color and the second color, to the third ultrasound transducer within a third housing measuring a third heart rate based on output of an ultrasound device in the third ultrasound transducer;
displaying a third heart rate indicator on a display device in association with the third transducer label;
identifying a third position of the third ultrasound transducer in the two-dimensional plane;
displaying the third transducer label on the abdomen image based on the third position to visually represent the placement of the third ultrasound transducer on the mother's abdomen; and
illuminating a third illumination device on the third housing in the third color to provide a visual association between the third ultrasound transducer and the third transducer label displayed on the abdomen image.

* * * * *